United States Patent
Wittmann et al.

(10) Patent No.: US 6,546,126 B1
(45) Date of Patent: Apr. 8, 2003

(54) METHOD FOR AUTOMATICALLY SETTING INTENSITY OF ILLUMINATION FPR POSITIONAL RECOGNION AND QUALITY CONTROLDE

(75) Inventors: Günther Wittmann, München (DE); Matthias Hedrich, München (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 09/446,485

(22) PCT Filed: Jun. 10, 1998

(86) PCT No.: PCT/DE98/01581

§ 371 (c)(1),
(2), (4) Date: Dec. 21, 1999

(87) PCT Pub. No.: WO99/01014

PCT Pub. Date: Jan. 7, 1999

(30) Foreign Application Priority Data

Jun. 27, 1997 (DE) .......................... 197 27 471

(51) Int. Cl.[7] .................................................. G06K 9/00
(52) U.S. Cl. ................................. 382/147; 250/559.46
(58) Field of Search ............................... 382/141, 145, 382/147, 149; 348/125–134, 87; 356/237.4, 237.5; 250/559.34, 559.39, 559.46

(56) References Cited

U.S. PATENT DOCUMENTS

| 5,185,811 A | 2/1993 | Beers et al. ............... 382/8 |
| 5,454,049 A | 9/1995 | Oki et al. ................. 382/172 |
| 6,005,977 A | * 12/1999 | Tanimizu et al. .......... 382/141 |

FOREIGN PATENT DOCUMENTS

| JP | 62-299948 | 12/1987 |
| JP | 8-152311 | 6/1996 |
| WO | WO 96/21343 | 7/1996 |

OTHER PUBLICATIONS

Patent Abstracts of Japan, vol. 096, No. 011, for Japanese Pub. No. 8–189901, Jul. 23, 1996.
Patent Abstracts of Japan, vol. 017, No. 522 for Japanese Pub. No. 5–141921, Jun. 8, 1993.

* cited by examiner

*Primary Examiner*—Brian Werner
*Assistant Examiner*—Shefali Patel
(74) *Attorney, Agent, or Firm*—Harness, Dickey & Pierce, PLC

(57) ABSTRACT

A method for automatically setting illumination intensity of light sources used within either positional recognition devices or quality control devices that, in turn, are used in devices that automatically equip components on a printed circuit board or ceramic substrates. The individual light sources are successively varied and an image of a component to be placed on a printed circuit board or substrate is registered by a camera. The resulting picture elements are registered as grayscale values and stored in an image evaluation unit. The grayscale values are either represented as useful structures of the component or unwanted structures of the component dependent on the illumination intensity of the individual light sources. The stored grayscale values for all of the light sources are summed according to respective useful and unwanted structures of the component and then compared to one another. Using a linear optimization methodology, either maximum or minimum difference values are set dependent on whether the difference between the grayscale value sums of the useful and unwanted structures yield a large difference value. The illumination and intensities of the light sources are set at an optimum illumination and intensity based on either the maximum difference or minimum difference.

16 Claims, 1 Drawing Sheet

METHOD FOR AUTOMATICALLY SETTING INTENSITY OF ILLUMINATION FPR POSITIONAL RECOGNION AND QUALITY CONTROLDE

BACKGROUND OF THE INVENTION

The invention is directed to a method for automatically setting illumination intensity for positional recognition devices and quality control devices during automatic placement of components on a printed circuit board or ceramic substrate.

When automatically equipping printed circuit boards or ceramic substrates with components, particularly surface mounted device (SMD) components, the position of the components relative to the placement position on the printed circuit board is identified before mounting the components using means for positional recognition. All articles capable of being equipped, for example shielding plates as well, are covered below by the term components. Optical system, comprised of a camera (e.g., a CCD camera), an illumination means are generally utilized as positional recognition devices. Visual inspection of the components ensues in analogously constructed devices for quality control. Illumination for these devices is selected such that useful structures (generally the terminals of the components) are shown with extremely high contrast, whereas unwanted structures (for example the body of the components) are suppressed.

Methods are known for the above purposes wherein the components are eliminated from different angles with different intensities with the assistance of illumination devices that are subdivided into a plurality of light sources each having a respectively separately controllable intensity.

JP 8-152311 (A), for example, discloses the illumination of soldered connections from different directions in order to inspect the quality of the soldered connections. The grayscale values identified in the individual illuminations are summed in an image evaluation unit. However, no teaching is given the document as to how illumination can be realized in an automatically adjustable way.

WO 96/21343, as another example, discloses a method wherein the components are not uniformly illuminated from all angles with the assistance of segmented ring illumination. Rather, no light is incident onto the structure from specific angles. Imagings of unwanted structures that may particularly emerge from these specific angles are thus suppressed.

A disadvantage of the known methods using a plurality of light sources is that an optimum illumination for the component must be manually set by an operator for each new component. To that end, the intensities of the individual light sources must be regulated by the operator until, under visual supervision, he has achieved an illumination adequate for the positional recognition or quality control. Hence, intensity setting in these known methods is user-specific and not reproducible, as would be required for equipping numerous circuit boards with large numbers of components.

U.S. Pat. No. 5,454,049 discloses a method for automatically setting illumination light source, wherein grayscale values registered with a camera and stored in an image evaluation unit are modified by an intensity control means such that the existing grayscale range of the image evaluation unit is optimized. However, this method is not suitable for illumination with a plurality of light sources, since the influence of the intensities of the individual light sources is not taken into consideration.

SUMMARY OF THE INVENTION

The present invention featured a reproducible, automatic method with which the intensity setting of the illumination is assured without fault in other-words at least two light sources used for positional recognition and quality control during equipping of a printed circuit board or substrate with components.

In order to achieve these features, the present invention includes a method for automatically setting illumination intensity for positional recognition devices and quality control devices used in automatic devices for placing components. Each of the positional recognition and quality control devices includes at least two or more light sources controlled by respective intensity control devices, a camera for registering an image of a component to be placed and an image evaluation unit connected to the camera that rasters the image of the component into picture elements in the form of grayscale values and registers at least a portion of the registered image. Further, picture elements of the image are divided into elements representing useful structures of the component and unwanted structures of the component. These respective structure elements are then allocated within the image evaluation unit to represent useful and unwanted structures.

The method includes these steps of successively eliminating the component according to varied illumination intensities by each respective light source. The image;of the component is then registered with the camera for each successive illumination. Grayscale values of the image registered by the camera are stored as grayscaled value parts in the image evaluation unit and respectively allocated as either representing useful structures or unwanted structures of the component, wherein the grayscale value ranges of the useful and unwanted structures are identified dependent on the illumination intensity of the individual light sources. The stored grayscale value parts are then summed in the evaluation unit for all of the light sources according to both the useful and the unwanted structures of the component, respectively. The respective grayscale values sums of the unwanted structures are then compared to the grayscale values of the useful structures.

Determination is then made whether the useful structures can be distinguished from the unwanted structures by identifying whether the difference between the grayscale:value sums of the unwanted and useful structures yields a substantially large difference. When at least one light source yields a substantial large difference between the grayscale value sums of the unwanted and the useful, structures, a desired maximum difference value is established. If the difference between the grayscale value sums does not yield a substantially large difference, a desired minimum difference value is-established. The difference values, whether maximum or minimum, are established utilizing a linear optimization. Finally, the illumination and intensities of the light sources are set at an optimum intensity based-on either the maximum difference value or the minimum difference value.

Compared to the known methods, the inventive method offers the advantage of achieving an automatic illumination setting that sequences independent of a user and in an automated fashion, (i.e., without involved, time-consuming trials) assuring a faultless illumination of a component in devices for positional recognition and quality control within an automatic equipping unit.

Additional advantages and novel features of the invention will be set forth in part in the description that follows and, in part, will become apparent to those skilled in the art upon examination of the following or may be learned by practice of the invention. The advantages of the present invention may be realized and attained by means of instrumentalities and combinations particularly pointed out in the appended claims.

BRIEF DESCRIPTION OF THE DRAWINGS

Reference is made to the attached drawings, wherein elements having the same reference numeral represent like elements throughout and wherein.

DESCRIPTION OF THE PREFERRED EMBODIMENTS

Figure 1:
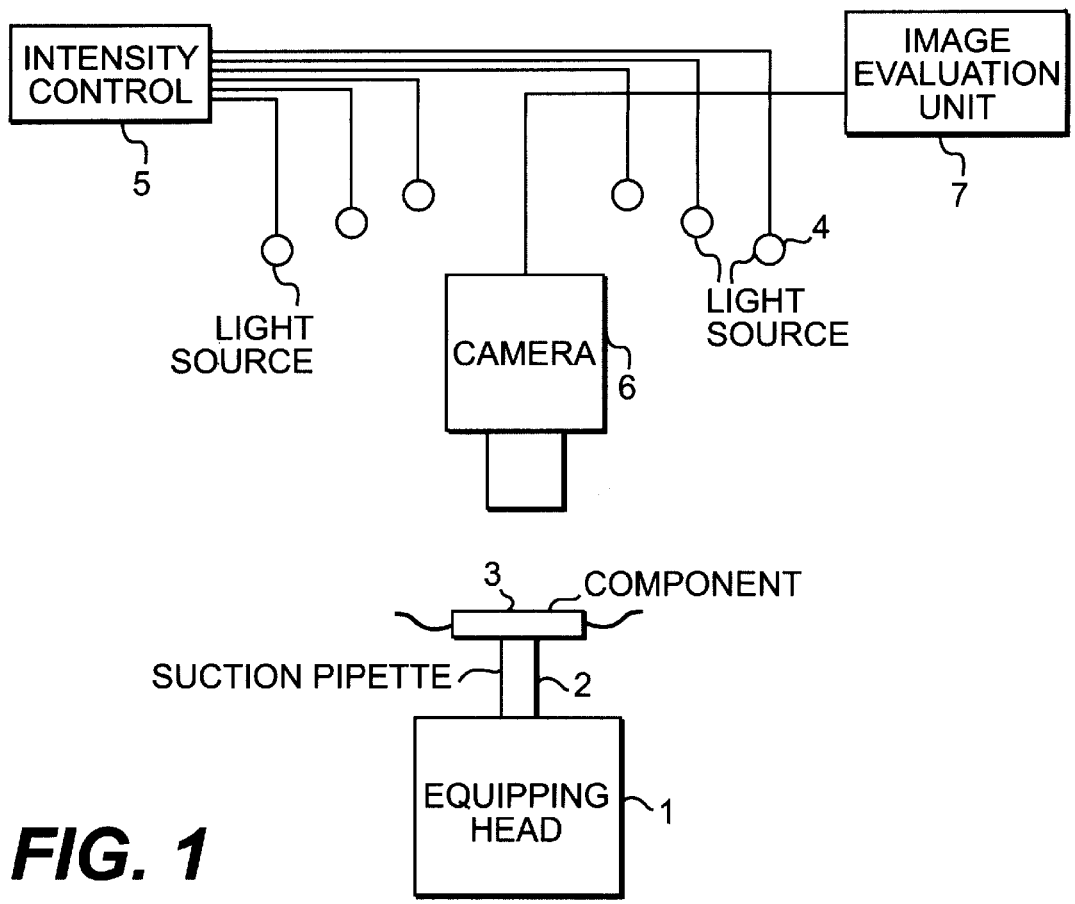
FIG. 1 is an illustration of an apparatus used by the present method for automatically setting intensity of illumination within either positional recognition device or a quality control device.
Figure 2:
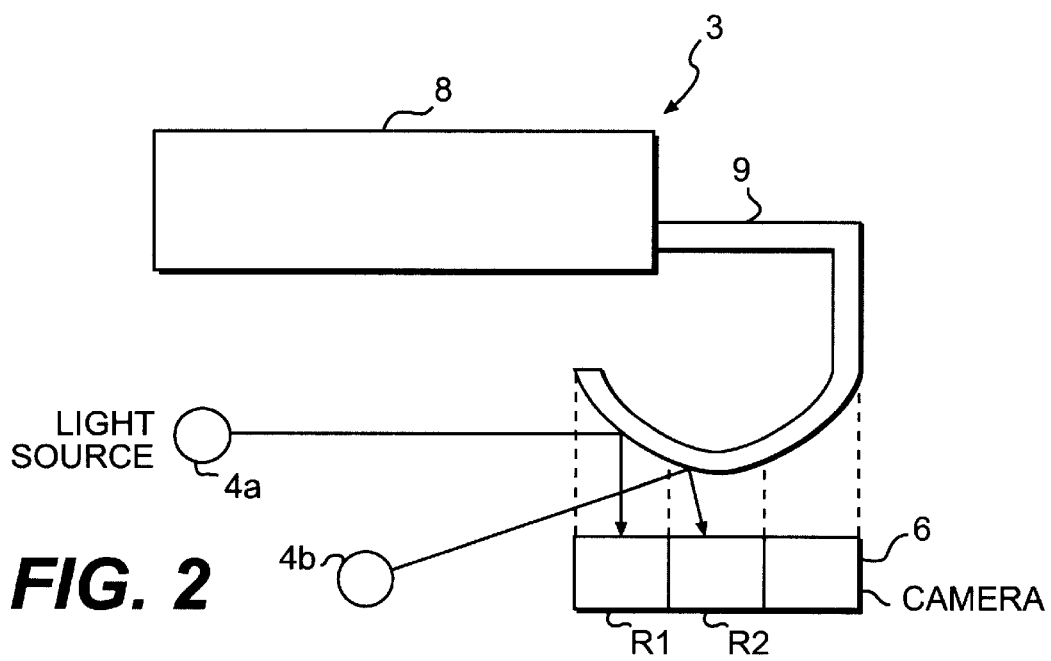
FIG. 2 illustrates the operation of the device of FIG. 1 when component leads have non-linear surfaces according to embodiments of the present invention.

In an automatic equipping unit for equipping a printed circuit board, as illuminated in FIG. 1 components 3 are picked up from supplied containers by a suction pipette 2 secured to an equipping head 1 and are investigated by a positional recognition means for their relative position at the suction pipette 2, in that the components 3 are illuminated by an illumination means composed of a plurality of light sources 4. The intensity of each light source 4 can be separately controlled by an allocated intensity control means 5. The image of the component 3 is registered by a camera 6 and an image evaluation unit 7 and is stored in the image evaluation unit 7. Work is usually performed with a CCD camera, whose smallest resolution is called a pixel. A grayscale value is allocated to each pixel, whereby a higher grayscale corresponds to a greater brightness. Given the employment of a color camera, values are stored that correspond to the detected color. These values are likewise referred to below under the term of grayscale value, since the inventive method is equally suitable for color cameras as well. By comparing the registered position of the terminals 9 or, in other words the useful structures 9 of the components 3 as shown in FIG. 2 to stored comparison patterns, the image evaluation unit 7 can recognize the current position of the component 3 on the suction pipette 2, calculate a correction, and forward the correction to a central control unit (not shown) of the automatic equipping unit. Hence, the position of the suction pipette 2 or of the printed circuit board is correspondingly varied such that the component 3 is placed in the correct position on the printed circuit board.

In order to determine an unambiguous relationship between comparison patterns the registered image of the component 3, useful structures 9 (for example, terminals) must be imaged with high contrast along with the simultaneous suppression of unwanted structures 8 (for example, the body of the component 3), through the intensity setting of the illumination.

An exemplary embodiment of the method of the present invention achieves an optimum, automatic illumination setting in the means for positional recognition and quality control in that an allocation of the pixels of the camera to useful 9 and unwanted 8 structures of the component 3 is performed on the basis of a unit of the components 3 to be placed on the circuit board or substrate. The allocation may be performed, for example, on the basis of a theoretical description of the geometrical structure of the component 3 that is stored in the image evaluation unit 7 for example. A further possibility is the presentation of the registered image of the component 3 on a picture screen (not shown) connected to the image evaluation unit 7 with which an operator can visually identify useful 9 and unwanted 8 structure. The allocation then may be accomplished manually by the operator in that he identifies respectively allocated regions on the picture screen, these then being stored in the image evaluation unit 7. This possibility offers the advantage that a manual adjustment of the component 3 in the position recognition means belonging to the method can ensue during the course of the visual; identification of unwanted 8 and useful 9 structures.

The speed of the present method can be increased by reducing the resolution through combining a plurality of pixels to form what are referred to as "moxels". An average grayscale value is thereby allocated to the moxels by averaging the grayscale values allocated to the pixels.

The following values are subsequently determined according to the present method:

a) the maximum grayscale value $N_{max}$ of the useful structures 9, b) the average value N of the grayscale values of the useful structures 9, c) the minimum grayscale value $N_{min}$ of the useful structures 9, d) The maximum grayscale value $S_{max}$ of the unwanted structures 8, e) the average value S of the grayscale values of the unwanted structures 8.

Given illumination with a plurality i of light sources 4 with respective intensity $X_i$, the grayscale values are derived as a sum of respective grayscale value parts that are identified in the illumination with only one light source 4. Assuming that saturation effects in the camera are negligible, linear dependencies can be derived between the intensities $x_i$ of the individual light sources 4 and the grayscale value parts expressed by corresponding coefficients:

$a_{n,max,i}$ for maximum grayscale value parts of the useful structures 9;

$a_{n,i}$ for average values of the grayscale value parts of the useful structures 9;

$a_{n,min,i}$ for minimum grayscale value parts of the useful structures 9;

$a_{s,max,i}$ for maximum grayscale value parts of the unwanted structures 8; and $a_{s,i}$ for average values of the grayscale value parts of the unwanted structures 8.

The grayscale values indicated under items a) through e) on the previous page thus are derived as linear combinations of the coefficients and the corresponding intensities $x_i$ according to the following equations:

$$N_{max} = \sum_i (a_{n,max,i} \cdot x_i) \tag{1}$$

$$N = \sum_i (a_{n,i} \cdot x_i) \tag{2}$$

$$N_{min} = \sum_i (a_{n,min,i} \cdot x_i) \tag{3}$$

$$S_{\max} = \sum_i (a_{s,\max,i} \cdot x_i) \quad (4)$$

$$S = \sum_i (a_{s,i} \cdot x_i) \quad (5)$$

When the coefficients $a_{n,max,i}$, $a_{n,min,i}$, $a_{s,max,i}$ and $a_{s,i}$ are combined in line vectors $A_{n,max}$, $A_n$, $A_{n,min}$, $A_{s,max}$ and $A_s$ with i an $a_{ba}$ of columns and the intensities $x_i$ are combined into a column vector X having i rows, then equations (1) through (5) can also be written as scalar product of vectors:

$$N_{max} = A_{n,max} \cdot X \quad (6)$$

$$N = A_n \cdot X \quad (7)$$

$$N_{min} = A_{n,min} \cdot X \quad (8)$$

$$S_{max} = A_{s,max} \cdot X \quad (9)$$

$$S = A \cdot X \quad (10)$$

To determine the coefficients, the intensities $x_i$ of all light sources 4 are first set to a predetermined value, (e.g., equal to zero) the intensities $x_i$ of the individual light sources are successively varied and once again set to the predetermined value. The camera 6 then registers the image of the component 3 and the grayscale value parts for the intensities $x_i$ respectively set for the respective light sources are determined by the prior allocation of pixels (or, moxels) to unwanted 8 and useful 9 structures. By dividing the grayscale value parts by the intensities $x_i$ that have been set, the coefficients that are stored in the image evaluation unit 7 are derived.

For example, given six light sources 4, five coefficients have thus been determinated after the implementation of the measurement of the grayscale a value parts for each of the six light sources. With the assistance of a linear optimization, the optimum illumination can now be automatically determined from these thirty coefficients that have been identified.

In a first embodiment, limit values for the grayscale values or differences between them are initially defined. The difference of the maximum grayscale value $N_{max}$ of the useful structures 9 and the average value N of the grayscale values of the useful structures 9 should be lower than a predetermined, first limit value GW1 as represented in the following relationship $$N_{max} - N = (A_{n,max} - A_n) \cdot X \leq GW1 \quad (11)$$

The difference of the average value N of the grayscale values and the minimum grayscale value $N_{min}$ of the useful structures 9 should be smaller than a predetermined, second limit value GW2 according to the following relationship $$N - N_{min} = (A_n - A_{n,min}) \cdot X \leq GW2 \quad (12)$$

The difference of the maximum grayscale value $S_{max}$ and the average value S of the A grayscale values of the unwanted structures 8 should be smaller than a predetermined, third limit value GW3, according to the following relationship $$S_{max} - S = (A_{s,max} - A_s) \cdot X \leq GW3 \quad (13)$$

The average value N of the grayscale values of the useful structures 9 should be higher than a predetermined, fourth limit value GW4, according to the following relationship $$N = A_N \cdot X \geq GW4 \quad (14)$$

or $$-A_N \cdot X \leq -GW4 \quad (15)$$

The intensity should be greater than zero, which, after introduction of an auxiliary vector 1 with elements that have the units of intensity and the value 1, can be vectorially written:

$$1 \cdot X \geq 0 \quad (16)$$

or $$-1 \cdot X \leq 0 \quad (17).$$

By introducing a vector B and a matrix A, equations (11), (12), (13), (15), and (17) can be combined:

$$B = \begin{pmatrix} GW1 \\ GW2 \\ GW3 \\ -GW4 \\ 0 \end{pmatrix} \quad (18)$$

$$B = \begin{pmatrix} A_{n,\max} - A_n \\ A_n - A_{n-\min} \\ A_{s,\max} - A_s \\ -A_n \\ -1 \end{pmatrix} \quad (19)$$

$$A \cdot X \leq B \quad (20).$$

A subsequent check is made to see whether the useful structures 9 can be distinguished from the unwanted structures 8, this being the case when a substantially large difference between the coefficients $a_{n,1}$ and $a_{s,i}$ of the averages of the grayscale values of useful 9 and unwanted 8 structures occurs for at least one light source i according to the following conditions
positive contrast:

$$a_{n,1} \gg a_{s,i} \quad (21)$$

negative contrast:

$$a_{n,1} \ll a_{s,i} \quad (22)$$

What this generally expresses is that the grayscale value ranges of useful 9 and unwanted 8 structures have an adequately large spacing.

The optimization condition then reads that the difference between the average values N and S of the grayscale value of the useful 9 and of the unwanted 8 structures should be equal to a maximum value Max:

$$N - S = \text{Max} \quad (23)$$

or, correspondingly, (with a minimum value Min):

$$-(N-S) = \text{Min} \quad (24)$$

which, with the line vector C $$C = (A_n - A_s) \quad (25)$$

can also be written as:

$$-C \cdot X = \text{Min} \quad (26)$$

The spacing of the grayscale value ranges of unwanted 8 and useful 9 structures is thus selected to be optimally large.

When no light source i is found whose allocated coefficients of the average values of the grayscale values 9 of useful and unwanted 8 structures differ as greatly as in equations (21, 22), then useful and unwanted structures 9,8 cannot be separated.

In the event of this condition, the optimization condition utilized assumes the difference between the average values N and S of the grayscale values of useful 9 and unwanted 8 structures is a minimum value Min according to the equations:

$$N-S=\text{Min} \quad (27)$$

or, with equation (25):

$$C \cdot X = \text{Min} \quad (28).$$

The optimum illumination will then supply approximately identical grayscale values for useful 9 and unwanted 8 structures so that the position of the component 3 is recognized on the basis of the external shape of the component 3 against a background. The condition for the predetermined fourth limit value GW4 (equations 14 and 15) refers to the average value S of the grayscale values of the unwanted structures 8 in this case wherein:

$$S = A_s \cdot X \geq GW4 \quad (29)$$

or $$-A_s \cdot X \leq -GW4 \quad (30)$$

Equation (20) is correspondingly adapted in this case.

The distance between the grayscale value ranges of unwanted 8 and useful 9 structures thus becomes minimal.

Equations (20) and (26) or, equations (20) and (28) are solved with the assistance of a linear optimization method, for example a revised simplex algorithm (see, e.g., Bronstein, Semendjajew, Taschenbuch der Mathematik, 24th Edition, Harri Deutsch, publishers, Thun and Frankfurt/Main, pages 711 ff), within a program in the image evaluation unit 7 that sets the desired intensities $x_i$ of the individual light sources i at an optimum illumination level.

A second exemplary embodiment, as shown in FIG. 2, is especially suited for components 3 having 9 (i.e., the useful structure) having an actual terminal surface, wherein the image of the terminals 9 registered by the camera 6 is divided as useful structure 9 into regions R1, R2 that are separately investigated. An individual light source 4a or, 4b does not generate a uniform illumination of the useful structure 9. Rather, regional bright spots arise whereas the remainder of the useful structure 9 remains dark. The pixel or moxel having the maximum grayscale value of the structure is not fixed but changes with changing illumination direction due to different light sources 4a, 4b. For this reason, the difference between the maximum grayscale value $N_{max}$ and the average value N cannot be represented as linear combination of the intensity values $x_i$ or the light sources 4a, 4b. The analogous case also applies for the difference between the average value N and the minimum grayscale value $N_{min}$ as well as for the difference between the maximum grayscale value $S_{max}$ of the unwanted structure and the average value S.

In order to achieve a uniform presentation of the useful structures 9 (the analogous case applies to the unwanted structures 8), regional coefficients $a_{n,R1,i}$ $a_{n,R2,i}$ for the respective average value $N_{R1}$, $N_{R2}$ of the grayscale values of the useful structures 9 are identified in the respective regions R1, R2. Given two light sources 4a and two regions R1, R2, a total of four regional coefficients $a_{n,R1,i}$ $a_{n,R2,i}$ are identified. The plurality of light sources 4 and of regions R1, R2 can be varied dependent on the problem. The average values $N_{R1}$, $NR_2$ of the grayscale values in the regions R1, R2 analogously derive as linear combination of the regional coefficients $a_{n,R1,i}$ $a_{n,R2,i}$ and the intensities $x_i$ of the light sources 4a, 4b. It should be taken note of as boundary condition that the average values $N_{R1}$, $N_{R2}$ of the grayscale values of the regions R1, R2 are not greater than a fifth limit value GW5, so that the signal limitation of the camera 6 is not exceeded.

$$N_{R1}, N_{R2} \leq GW5 \quad (31).$$

In the determination of the coefficients $a_{n,1}$ for the average values $N_{R1}$, $N_{R2}$ of the grayscale values of the useful structure 9, it is assumed that all light sources 4a, 4b are utilized for illumination. Accordingly, the coefficients $a_{n,i}$ for the average values $N_{R1}$, $NR_2$ of the grayscale values of the useful structure derives as arithmetic average of the regional coefficients $a_{n,R1,i}$ $a_{n,R2,i}$.

The determination of the optimum illumination then ensues analogous to the described, first exemplary embodiment.

What is claimed is:

1. A method for automatically setting illumination intensity for positional recognition devices and quality control devices used in automatic devices for placing components, wherein each of the positional recognition and quality control devices include at least two light sources being controlled by respective intensity control devices, a camera for registering an image of a component to be placed and an image evaluation unit connected to the camera that rasters the image of the component into picture elements in the form of grayscale values and registers at least a portion of the registered image, wherein picture elements of the image of the component are divided into picture elements representing useful structures of the component and picture elements representing unwanted structures of the component and allocating the respective picture elements to represent useful and unwanted structures within the image evaluation unit the method comprising:

successively illuminating the component according to varying illumination intensities with each respective one of the at least, two light sources;

registering the image of the component with the camera for each successive illumination;

storing grayscale values of the image registered by the camera as grayscale value parts in the image evaluation unit and respectively allocating the grayscale values as representing useful structures and unwanted structures of the component, wherein the grayscale value ranges of the useful and unwanted structures are identified dependent on the illumination intensity of the individual light sources;

summing the stored grayscale value parts in the evaluation unit of all of the at least two light sources according to the respective useful and unwanted structures of the component;

comparing the respective grayscale value sums of the unwanted and useful structures of the component to one another;

determining whether the useful structures can be distinguished from the unwanted structures by identifying whether at least one light source of the at least two light sources yields a substantially large difference between the respective grayscale value sums of the unwanted and the useful structures;

establishing a desired maximum difference value between the grayscale value sums of the respective unwanted and useful structures using a linear optimization when at least one light source yields a substantially large difference between the respective grayscale value sums of the unwanted and the useful structures, and establishing a desired minimum difference value between the grayscale value sums of the respective unwanted and useful structures using the linear optimization when at least one light source does not yield a substantially large difference between the respective grayscale value sums of the unwanted and the useful structures; and setting the illumination intensities of the at least two light sources at an optimum illumination intensity based on one of the desired maximum difference value and the desired minimum difference value.

2. The method according to claim 1, wherein the grayscale value parts are at least one of averaged pixel-by-pixel and averaged over a plurality of pixels and are allocated to at least one of the at least two light sources and to the intensity of the at least one of the at least two light sources and are stored in the image evaluation unit.

3. The method according to claim 1, wherein a minimum grayscale value part of the useful structures is determined in the image evaluation unit for each light source and for each intensity that is set and coefficients of the minimum grayscale value part of the useful structures are identified and stored by dividing by the intensity that has been set, so that a minimum grayscale value of the useful structures can be determined by a linear combination of these coefficients and the set intensity of all light sources.

4. The method according to claim 1, wherein an average value of the grayscale value parts of the useful structures is identified in the image evaluation unit for each light source and each intensity that is set and coefficients of the average value of the grayscale value parts of the useful structures are identified and stored by dividing by the intensity that has been set so that the average value of the grayscale values of the useful structures can be determined by a linear combination of these coefficients and the set intensity of all light sources.

5. The method for automatic intensity setting of an illumination according to claim 1, wherein the useful structures are divided into at least two regions and an average value of the grayscale value parts for each of the respective regions of the useful structure is identified in the image evaluation unit for each light source and each intensity that is set and regional coefficients of the average value of the grayscale value parts of the useful structure are identified and stored by dividing with the intensity that has been set so that an average value of the grayscale values of the regions of the useful structures can be determined by a linear combination of the regional coefficients and the set intensity of all light sources.

6. The method according to claim 5, wherein a maximum grayscale value part of the useful structures is identified in the image evaluation unit for every light source and every set intensity and coefficients of the maximum grayscale value part of the useful structures are identified and stored by dividing by the set intensity of the maximum grayscale value part of the useful structures so that a maximum grayscale value of the useful structures can be determined by a linear combination of the coefficients and the set intensity of all light sources.

7. The method according to claim 6, wherein the coefficients of the average value of the grayscale values of the useful structures is determined by the average value formation from the regional coefficients.

8. The method according to claim 1, wherein a maximum grayscale value part of the useful structures is identified in the image evaluation unit for every light source and every set intensity and coefficients of the maximum grayscale value part of the useful structures are identified and stored by dividing by the set intensity of the maximum grayscale value part of the useful structures so that a maximum grayscale value of the useful structures can be determined by a linear combination of the coefficients and the set intensity of all light sources.

9. The method according to claim 1, wherein a maximum grayscale value part of the unwanted structures is identified in the image evaluation unit for each light source and each set intensity and coefficients of the maximum grayscale value part of the unwanted structures are identified and stored by dividing by the set intensity so that a maximum grayscale value of the unwanted structures can be determined by a linear combination of the coefficients and the set intensity of all light sources.

10. The method according to claim 1, wherein an average value of the grayscale value parts of the unwanted structures is identified in the image evaluation unit for each light source and each set intensity and coefficients of the average value of the maximum grayscale value parts of the unwanted structures are identified: and stored by dividing by the set intensity so that an average value of the grayscale values of the unwanted structures can be determined by a linear combination of these coefficients and the set intensity of all light sources.

11. The method according to claim 10, wherein the coefficients of the average values of the grayscale value parts of the useful and of the unwanted structures are compared to one another with respect to individual light sources such that, when a light source exists whose allocated coefficients of the average values of the grayscale values of useful and unwanted structures greatly differ, an optimally great difference of the average values of the grayscale values of useful and unwanted structures is selected as an optimization condition and when a light source does not exist having allocated coefficients that greatly differ an optimally small difference of the average values of the grayscale values of useful and unwanted structures is selected as the optimization condition.

12. The method according to claim 1, wherein boundary values for the grayscale values and for the difference of quotients of grayscale values are prescribed.

13. The method according to claim 12, wherein at least one of boundary conditions for the difference between the maximum grayscale value and the average value of the grayscale values of the useful structures, for the difference between the average value of the grayscale values and the minimum grayscale value of the useful structures for the difference between the maximum grayscale value and the average value of the grayscale values of the unwanted structures, for the average value of the grayscale values of the useful structures and for the intensities is set with the prescribed boundary values.

14. The method according to claim 13, wherein a linear equation system is formed from the boundary conditions and optimization conditions; and in that the linear equation system is solved with the assistance of the linear optimization in the image evaluation unit.

15. The method according to claim 14, wherein a revised simplex algorithm is employed as a method for the linear optimization.

16. The method according to claim 12, wherein at least one of the boundary conditions for the average values of the grayscale values of the regions of the useful structures, for the average value of the grayscale values of the unwanted structures and for the intensities is set with the prescribed boundary values.

* * * * *